United States Patent [19]
Turner

[11] Patent Number: 5,097,844
[45] Date of Patent: Mar. 24, 1992

[54] HYPERTHERMIA APPARATUS HAVING THREE-DIMENSIONAL FOCUSING

[75] Inventor: Paul F. Turner, North Salt Lake, Utah

[73] Assignee: BSD Medical Corporation, Salt Lake City, Utah

[21] Appl. No.: 269,631

[22] Filed: Nov. 10, 1988

Related U.S. Application Data

[63] Continuation-in-part of Ser. No. 935,936, Nov. 28, 1986, Pat. No. 4,798,215, which is a continuation-in-part of Ser. No. 590,030, Mar. 15, 1984, Pat. No. 4,672,980, which is a continuation-in-part of Ser. No. 405,947, Aug. 6, 1982, Pat. No. 4,638,813, which is a continuation of Ser. No. 136,506, Apr. 2, 1980, Pat. No. 4,462,412.

[51] Int. Cl.$^5$ ............................................. A61N 5/00
[52] U.S. Cl. .................................... 128/804; 128/399; 128/736
[58] Field of Search ........................ 128/804, 399, 736

[56] References Cited

U.S. PATENT DOCUMENTS

| | | | |
|---|---|---|---|
| 4,572,190 | 2/1986 | Azam et al. | 128/399 |
| 4,589,424 | 5/1986 | Vaguine | 128/804 |
| 4,702,262 | 10/1987 | Andersen et al. | 128/804 |
| 4,815,479 | 3/1989 | Carr | 128/804 |
| 4,934,365 | 6/1990 | Morgentheler | 128/804 X |

FOREIGN PATENT DOCUMENTS

| | | | |
|---|---|---|---|
| 2420883 | 11/1975 | Fed. Rep. of Germany | 128/804 |
| 8102841 | 10/1981 | World Int. Prop. O. | 128/804 |

*Primary Examiner*—Lee S. Cohen
*Attorney, Agent, or Firm*—Mallinckrodt & Mallinckrodt

[57] ABSTRACT

A hyperthermia apparatus having a three-dimensional target positioning capability is disclosed. The apparatus includes a signal modifier, having electromagnetic power splitting, phase adjusting, and power gain capabilities, connected to a plurality of power connector assemblies having individual antenna power and power phase adjusting capability. The power connector assemblies connect power at preselected phases to a plurality of antenna groups forming an applicator. Each antenna group includes three antennae preferably of the dipole type stacked end to end on a tube of dielectric material. The phase of the power applied to the three antennae of the antenna groups is selected to provide a target heating spot positionable or adjustable in size in a body portion in a direction along the long axis of the body portion and within the cross-section perpendicular to the long axis. This adjustable size and positioning of the target along the long axis provides an additional dimension to the capability of moving the target perpendicular to the long axis in either direction from the center as provided in known applicators.

22 Claims, 10 Drawing Sheets

3D CYLINDRICAL DIPOLE ARRAY

HYPERTHERMIA APPARATUS HAVING THREE-DIMENSIONAL FOCUSING

The present application is a continuation-in-part of United States patent application for Letters Patent, Ser. No. 935,936 filed Nov. 28, 1986, (now U.S. Pat. No. 4,798,215 issued Jan. 17, 1989) which is a continuation-in-part of United States patent application Ser. No. 590,030 filed Mar. 15, 1984 (now U.S. Pat. No. 4,672,980 issued June 16, 1987), which is a continuation-in-part of United States patent application Ser. No. 405,947, filed Aug. 6, 1982 (now U.S. Pat. No. 4,638,813 issued Jan. 27, 1987), which is a continuation of patent application Ser. No. 136,506 filed Apr. 2, 1980 (now U.S. Pat. No. 4,462,412 issued July 31, 1984).

BACKGROUND OF THE INVENTION

This invention relates to a hyperthermia apparatus and more particularly to an apparatus having three-dimensional (3-D) focusing capability with combined hyperthermia treatment and noninvasive thermometry capabilities.

Known hyperthermia treatment systems include multiple applicators and multiple temperature sensors for controlling the operation of the hyperthermia system. The multiple applicators utilizing ultrasound or electromagnetic energy in the direct contact operating mode are placed directly upon an elastic cooling belt containing a circulating cooling liquid to carry the heat of hyperthermia treatment away from the surface of the healthy tissue. The temperature sensors are implanted in the normal tissue in the vicinity of the tumor, as well as within the tumor. Systems involving the placement of temperature sensors within the body are referred to as invasive thermometry systems. Those persons skilled in the art desiring additional information for this system are referred to U.S. Pat. No. 4,397,314 issued Aug. 9, 1983.

A known instrument for detecting microwave energy and for giving an accurate measurement of the power density thereof is disclosed in U.S. Pat. No. 3,919,638 issued Nov. 11, 1975. This instrument is substantially unaffected by polarization or modulation of the electromagnetic waves and includes a planar array of parallel connected diode detectors each having a pair of antenna leads forming a dipole antenna. The diode array may include groups of diodes having different antenna lead lengths to detect different frequencies of microwave energy for a meter. The meter may be selectively switched between the outputs of the different groups.

Further, the potential use of multiple frequency band radiometry as a means of noninvasive sensing of one-dimensional temperature profiles is presented in an article entitled "Noninvasive Thermometry Using Multiple-Frequency-Band Radiometry: A Feasibility Study", Stavros D. Prionas and G. M. Hahn, Bioelectromagnetic 6:391-404, 1985 Alan R. Liss, Inc. The article discloses that microwave thermography has been extensively used for the detection of cancerous nodules. Operating frequencies in the range of 1.3 to 6.0 GHz (free space wavelengths in the range of 5 to 23 cm.s) have been employed. At these long wavelengths subcutaneous temperature measurement is possible and detection of superficial tumors in the brain and thyroid is, in principle, feasible.

The article further discloses that a computer tomographic approach using 10 GHz microwaves has been proposed as an alternative to mammographic examination. A self-balancing microwave radiometer for measuring the energy emitted from a heated volume within a single frequency band has been developed at the RCA laboratories. The power spectrum of thermal noise generated by a given temperature depth distribution is governed by Planck's law of blackbody radiation. The frequency spectrum of energy received at the surface of the human body is affected by the frequency dependent attenuation properties of the intervening tissues. Microwave radiometry (the technique of measuring noncoherent electromagnetic energy, in the microwave part of the spectrum, that is emitted or scattered by the medium under observation) can be used to measure the thermal noise emitted from a heated volume of biological tissue.

This article reports the analysis of the spectral content of this thermal noise and the comparison of the magnitude of the signal to the inherent threshold of noise detectability associated with an ideal microwave radiometer. In the analysis a one-dimensional temperature distribution model was assumed. In real situations, three-dimensional temperature distributions will be encountered. It is clear that to resolve such a three-dimensional temperature field with a reasonable amount of spatial resolution additional information will be needed. This additional information might be in the form of data acquired using different orientations of a signal receiving aperture or a properly phased array of receiving apertures. An intriguing alternative is to employ a phased array of receiving apertures that coherently detect the signal emanating from a point in space. In either case, well established signal processing algorithms could be used to convert the measured data to reconstruct the temperature distribution.

The use of "Radiometer Receivers for Microwave Thermography" was disclosed in an article of the same title by D. V. Land, University of Glasgow, Glasgow, Great Britain, published in the microwave journal, May 1983. A comparison or Dicke radiometer configuration is used. The receiver produces an output from the input switching that is proportional to the difference between the source temperature detected by an antenna and the temperature of an internal reference load or noise generator.

Finally, the application of broad-band correlation techniques to medical microwave thermography was studied and reported in an article entitled "The Thermal and Spatial Resolution of a Broad-Band Correlation Radiometer with Application to Medical Microwave Thermography", Joseph C. Hill et al., IEEE Transactions on Microwave Theory and Techniques, Vol. MTT-33, No. 8, August, 1985.

An essential difference between the present invention and the invention of U.S. patent application Ser. No. 935,936, filed Nov. 11, 1986 and the background references is that the present invention is for a 3-D focusing of the energy which is accomplished by cylindrical or annular phased array. The previous annular phased arrays were capable of steering the heating pattern within the patient cross-section (target) with either power or phase steering. This feature was a primary function which resulted from the unique focusing provided by the coherent or at least synchronous EM fields which provided common polarization alignment of the electric field (E-field). The E-field in the target is the mechanism which creates the heating of the tissues. In contrast, the present invention uses at least an antenna group of at least three antennae stacked along the E-field direction and aligned with the long axis of the target. Thus, in a dipole configuration, the dipole lengths are aligned with the long axis of the target around which it is placed. This arrangement permits the heating fields to be not only focused and steered along the patient's cross-section but also along the long axis of the target.

An advantage of the 3-D hyperthermia apparatus is that in its simplest form (a single group), it allows the phase of the antennae to be set to provide a desired heating length. Another advantage is that a plurality of groups can be utilized to provide deep target heating capability. Yet another advantage is the adjustment of the phase and power of each group's elements to regulate the position of the heating region in the target.

SUMMARY OF THE INVENTION

Accordingly it is an object of the present invention to provide an apparatus for producing 3-dimensional (3-D) focusing in a target of body tissue.

Another object of the invention is to provide an apparatus capable of 3-D focusing in a target deep within a body portion.

Briefly stated the hyperthermia apparatus having 3-D focusing constituting the subject matter of the invention consists of one or more groups of antennae, each group consisting of at least three antennae stacked along the body axis. The power directed to each element of the group or groups of antennae is adjusted in phase and amplitude to focus electromagnetic energy to form a desired heating pattern in a target location for heating a preselected target in a body anywhere within the boundaries of the apparatus.

BRIEF DESCRIPTION OF THE DRAWINGS

Other objects and features of the invention will become more readily apparent from the following detailed description when read in conjunction with the accompanying drawings, in which.

DESCRIPTION OF THE PREFERRED EMBODIMENTS

Figure 1:
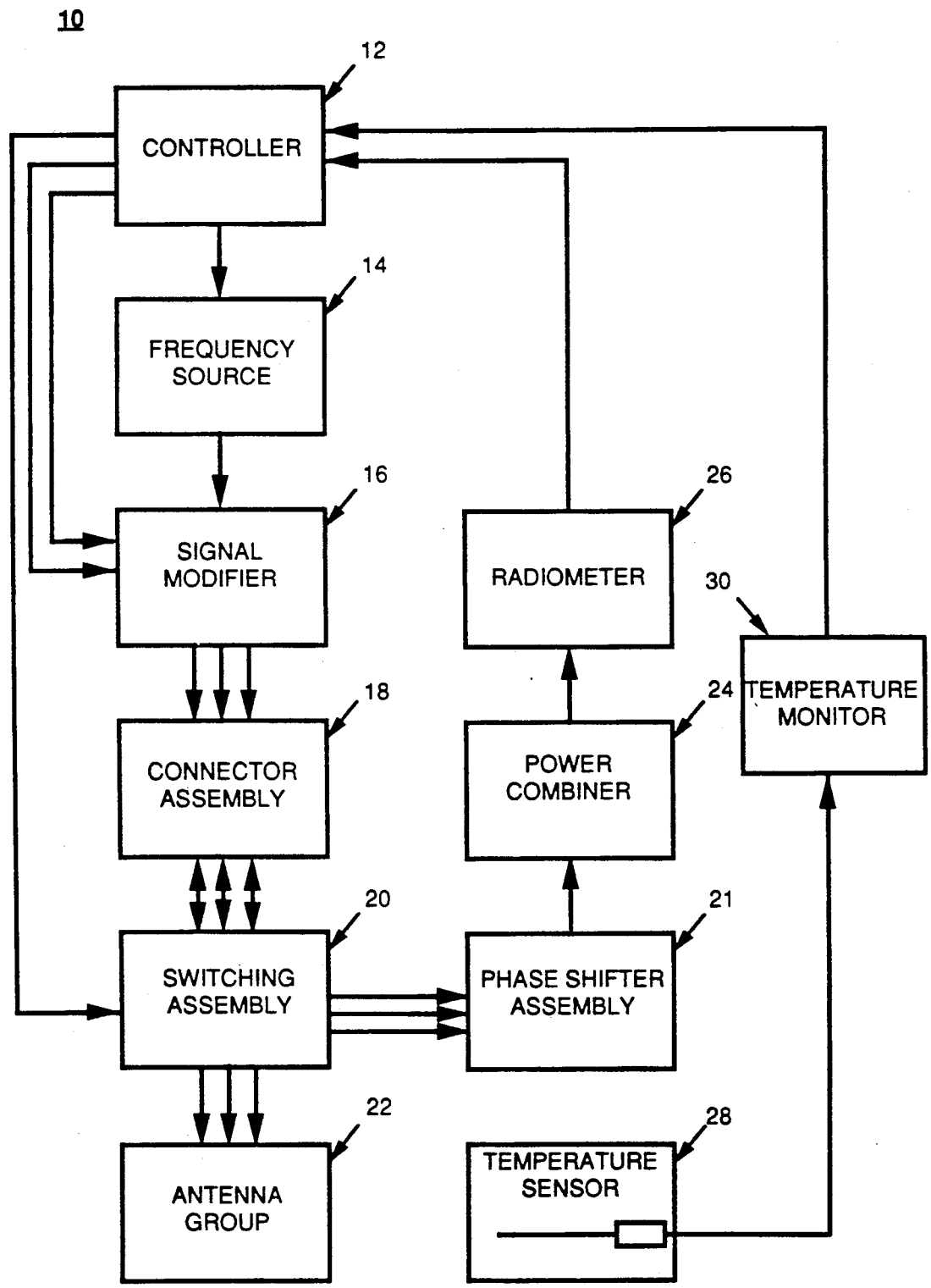
FIG. 1 is a schematic view in block form of the three-dimensional (3-D) hyperthermia system constituting the subject matter of the invention.

The three-dimensional (3-D) focusing hyperthermia system 10 (FIG. 1) includes a controller 12 connected to a frequency source of electromagnetic energy 14. The controller 12 is connected to a signal modifier 16 which includes as more particularly described hereinafter a power splitter and/or a plurality of amplifiers and phase shifters. The signal modifier 16 enables the modification of the phase and power amplitude of a multiple channel RF power system. A connector assembly 18 connects a switching assembly 20 to the signal modifier 16. The switching assembly 20 connects the connector assembly 18 to the antenna group or antenna groups 22 forming the applicator for the apparatus.

The radiometric circuit includes a phase shifting assembly 21 connected to the switching assembly 20 for directing the received signals generated from the body (blackbody radiation) to a power combiner 24 with equal or non-equal relative phase shift. A radiometer 26 is connected to the power combiner 24. The phase shift of the received signal enables the point of primary detection to be shifted to different regions within the body. This phase shifter may also include switches to eliminate or reduce the transfer of energy from certain ones of the antenna (dipole) elements. In this way it would enable the receipt of energy to favor certain dipole paths to a measure of more superficial tissue temperatures. Further, by activating at times only portions of these phase shifter channels, the tissue temperature around the surface region of the target tissue is measured noninvasively. The temperature measurements are made using the power detection capability of the radiometer. The radiometer 26 has its output connected to the controller 12 for controlling system operation. Power levels and phase of the signal modifier may be adjusted either by an operator or by a control loop to assure that the target tissue is maintained at the selected temperature and the non-target tissue is not overheated.

A temperature sensor assembly 28 of one or more temperature sensors are placed invasively into the tissue for measuring the temperature of the tissues being heated. Finally, a temperature monitor 30 is connected between the temperature sensor 28 and controller 12 for monitoring the temperature output signals of the temperature sensor assembly for the controller 12 to complete the system. Those persons skilled in the art are referred to the parent patent application, Ser. No. 935,936, filed Nov. 28, 1986 for additional information concerning the controller, radiometric circuit and temperature sensing circuit.

Figure 2:
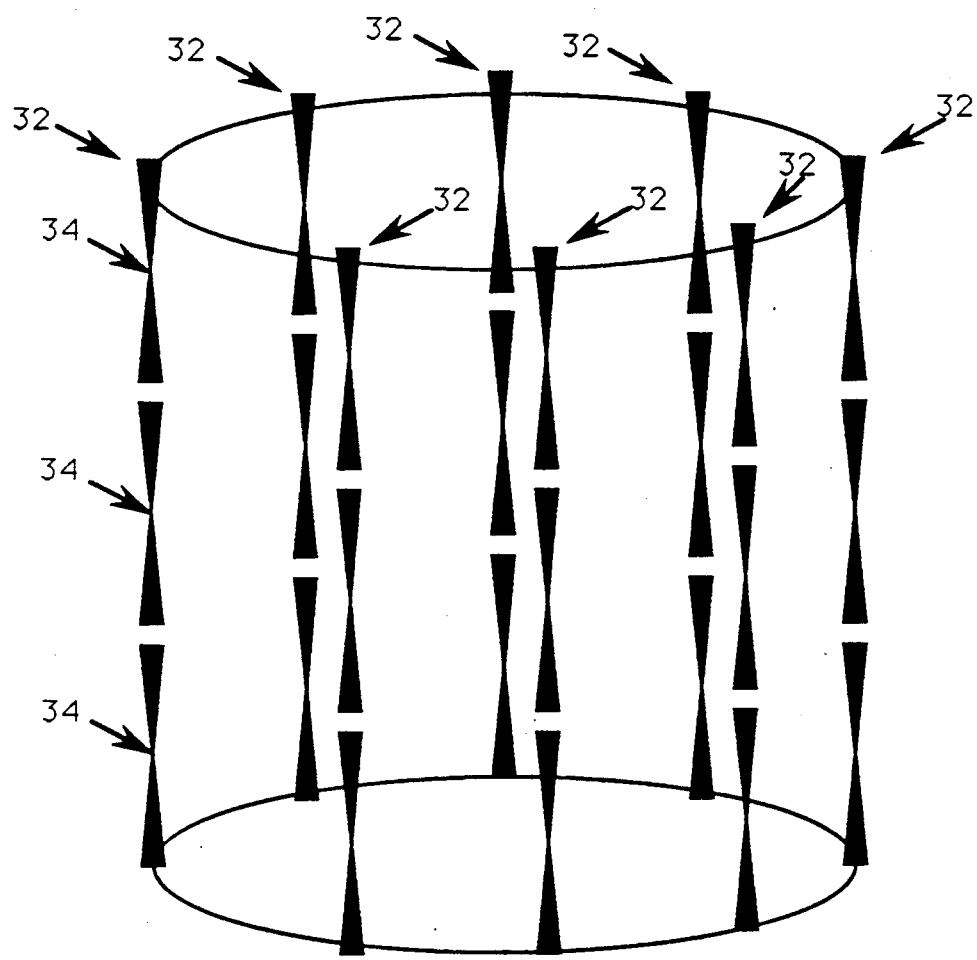
FIG. 2 is a view showing a cylindrical arrangement of groups of dipole antennae forming an electromagnetic applicator of the 3-D hyperthermia system.

Referring now to FIG. 2, the 3-D cylindrical dipole array consists of a plurality of groups 32 of antennae 34. Each group of antennae 32 includes at least three antennae 34 stacked end to end along the direction of the E-field polarization axis.

Numerical modeling studies show that little improvement is obtained when the number of antenna groups exceed eight. As the number of groups in the cylindrical shape decreases to fewer than eight, the depth of penetration begins to decrease. Nevertheless, the invention is not limited to eight antenna groups and any number of groups above or below eight are to be considered to be included in the invention.

It will be appreciated that the three stacked dipoles could be extended to include more dipoles and the phase of each could be controlled to provide proper phase alignment for target selection. If desired in connection with very complex arrays, a computer can be programmed in the controller to select the proper phase and power for each antenna. Although, for purposes of description and not by way of limitation, dipole type antennae are used throughout the description, the types of antennae may include patch, metal strips, metallic waveguide, dielectric waveguides, resonant cavities, coaxial antennae TEM mode horn types to name but a few types which can be used in practicing the invention.

The dipole antennae are preferably made of tapered metallic conductive strips with the feed located midway between the two strips forming the dipole. The taper is increased outwardly from the central feed point to increase the frequency bandwidth and the near field energy along the region of the tips of the dipoles. The length of the dipoles should be determined in light of the operating frequency to prevent loss of energy.

Figure 5:
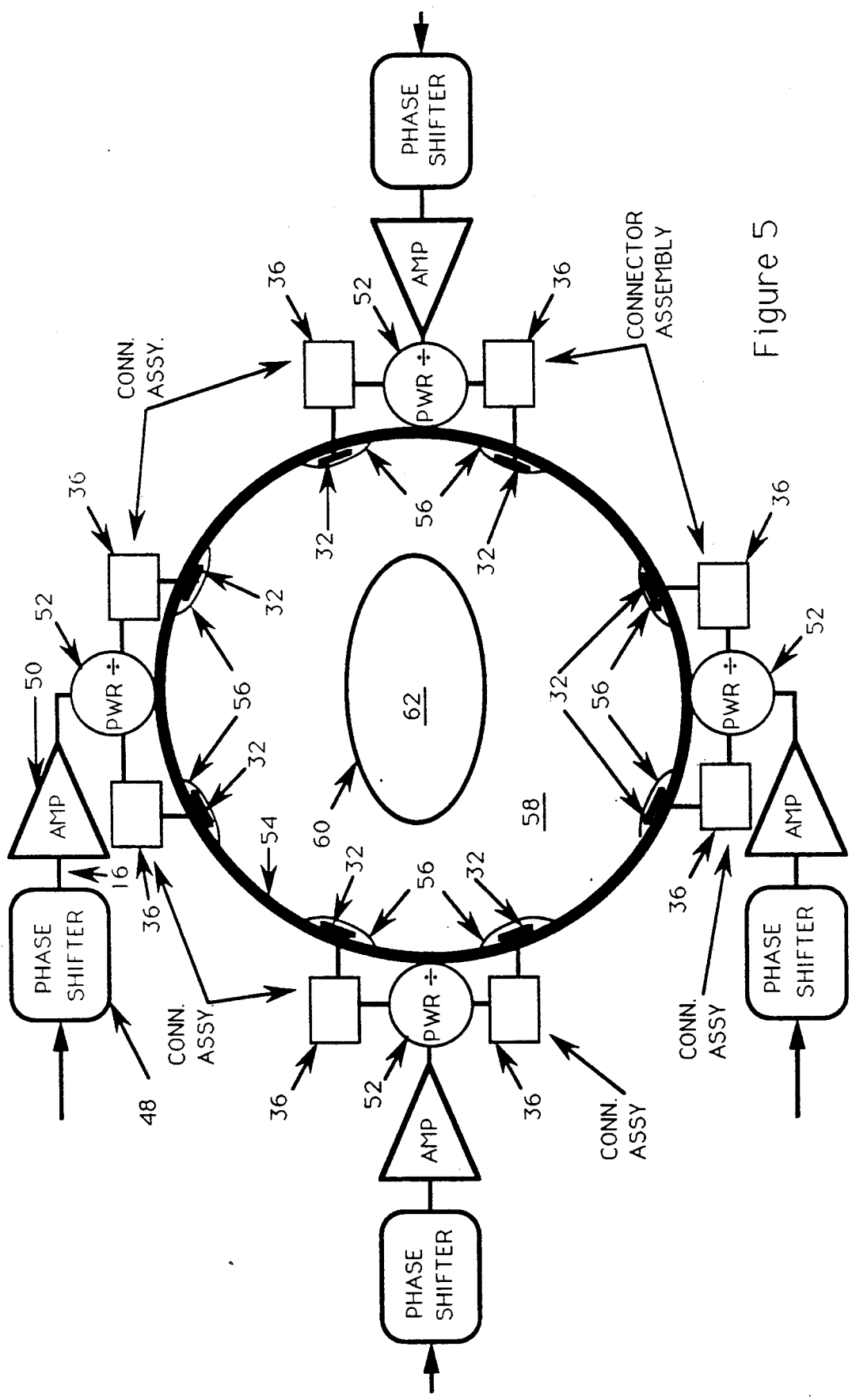
FIG. 5 is a view including a partial schematic in block diagram showing a first power connector arrangement for the groups of dipole antennae of FIG. 2 and a plan view of the applicator.

As shown in FIG. 5, these dipole groups 32 are formed normally along the inside wall of a clear plastic or dielectric cylinder 54 using well known adhesives or metal deposition processes. A thin patch of dielectric coating material 56 is used to cover the antennae groups 32. A bolus 58, can be formed with the cylinder by attaching a membrane 60 having sealed ends to the cylinder 54. A fluid input/output valve can be mounted in the cylinder 54 for inflating the bolus with the fluid. The inflated bolus defines the body area 62, provides tissue cooling, energy confinement, and improves antenna group coupling to the tissue. The fluid is a high dielectric low loss media such as deionized water.

The bolus has been included in other applicators. Nevertheless, in practicing this invention it is important to take into account the dielectric characteristics of the bolus region and the body as well when planning the activation phase of the individual antenna elements 34, FIG. 2 of antenna groups 32.

The normal operating frequency range for this system for the torso portion of an adult is between about 50 to 1000 MHz. It is most useful between 60 to 220 MHz where the penetration characteristics of the body are deeper. The lower frequencies however have larger wavelengths and limit the precision to which the tissue can be selectively heated. The phase of the dipoles determines the location of a focal point within the body. As dipoles have a wide pattern the focal point is where the same phases exist in the overlapping beams. At the other points in the overlapping beams the phase is different and the energy partially cancels. The typical size of the focal point defining the target in the body is about 30 to 50% of the wavelength within the tissue into which the electromagnetic energy is directed. The wavelength is inversely proportional to frequency. For example, at 100 MHz the wavelength in the high water tissues of the body is 27 cm.s and in deionized water is 30 cm.s. This similarity simplifies a rough estimate for planning the required phase activation for a certain focal zone because of the similar size. For example, the focal size of the 100 MHz EM energy within the high water content tissue is between 9 to 14 cm.s in diameter.

From the above, it is readily apparent that if the operation frequency is changed to 200 MHz the focal diameter would change to about 4.5 to 7 cm.s for a wavelength of 14 cm.s in the high water tissues. While changing the frequency provides higher precision for the focusing, the penetration depth is less than that for 100 MHz. For 100 MHz operation the dipole, if the dipole length is one-half of a wavelength within the water media, should be an efficient radiator having a length of about 15 cm.s; if a dielectric coating is placed over the dipoles the operating frequency may need to be increased.

Figure 3:
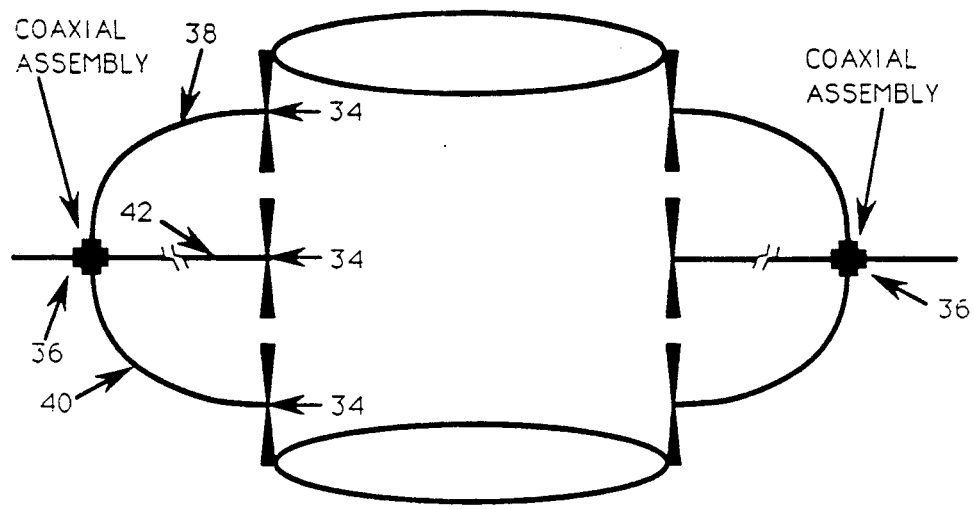
FIG. 3 is a partial schematic view showing in block form a first power connector arrangement for the dipoles of at least two dipole antenna groups.

A first embodiment of the connector assembly 18 for each antenna group 32 is shown in FIG. 3. As the connectors of the connector assembly are identical only two of the antenna groups 32 are shown and one described for clarity and brevity of the description. Thus, each connector 36 includes a coaxial cable connected between the signal modifier 16 (FIG. 1) and a tee. The tee 36 is connected to coaxial cables 38, 40 and 42. The coaxial cables 38 and 40 have substantially identical lengths for providing power at the same phases to the end antennae 34. While, coaxial cable 42 has a longer length to compensate for the shorter distance from the central dipole and the central focus point.

In a second embodiment of the connector assembly 18 (FIG. 4), a power divider 44 is connected to the signal conditioner. Coaxial cables 38 and 40 interconnect the outer power divider outputs to the outer dipoles 34. A phase shift module 46 interconnects the center output of the power divider to the center dipole of dipoles 34. Again, if the cables 38 and 40 have the same length, the phase shift module can be set to provide an operation equivalent to the first embodiment; however, the phase of the phase shift module is variable for adjusting the size of the heating field along the long body axis. This is the result of the phase focusing within the primary target zone and the destructive phase cancelling which occurs from the different phase in the regions displaced from the phase focus. This destructive or cancelling phase is the result of the different path lengths to the non-target point resulting in the partial cancelling of the energy within these off target areas. When the control antennae radiated phase to the center is set to be different from the outer antennae, the heating length is increased. This also causes a reduced intensity of the power to the center tissue. This can cause higher reductions in the surface heating levels as compared to that within the central region, and is most effective when the phase shifts of the central antennae are caused to lead the maximum focus values of phase for the other antennae. Thus, this embodiment represents the full steering capability of the system, and the variable used to optimize a treatment utilizes proper selection of the phase and power to each dipole at a selected frequency. When eight groups of three dipoles are used it is preferred that they be activated by a signal modifier which includes power splitters, phase shifters and a four, eight, sixteen, or twenty-four channel amplifier.

Referring to FIG. 5, when the signal modifier 16 includes a four channel amplifier, a four-way power divider is generally used to divide the power from the controller 12. The signal modifier 16 includes four circuits each including a phase shifter 48, amplifier 50 and a two-way power divider 52. The phase shifter 48 is connected to the power divider or power source for controlling the phase of the power applied to an amplifier 50. Amplifier 50 provides the increase in signal power (gain) necessary for the pair of adjacent dipole groups 32. While the power divider 52 divides the amplified power for input to the connector assemblies 36 connected to each dipole group 32. The connector assemblies are those described in connection with FIGS. 3 and 4.

Figure 4:
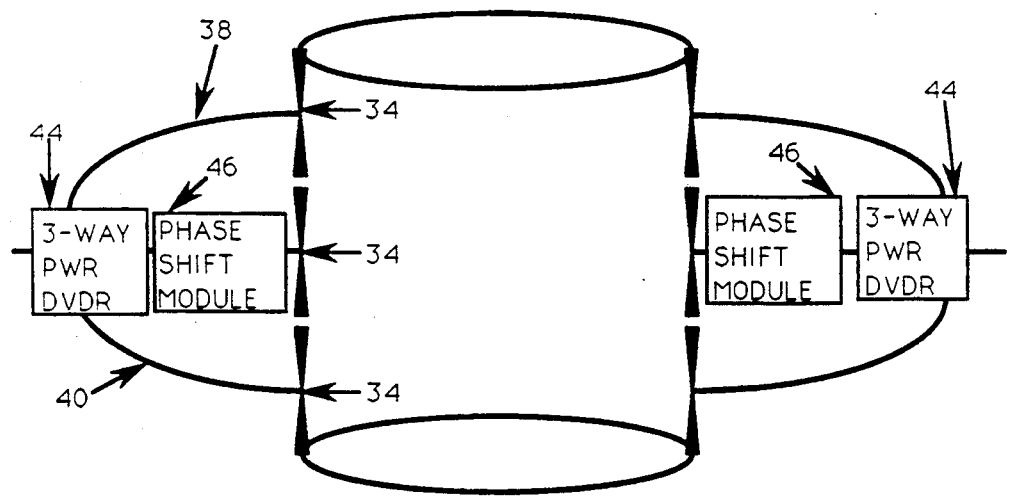
FIG. 4 is a partial schematic view showing in block form a second power connector arrangement for the dipoles of at least two dipole antenna groups.
Figure 6:
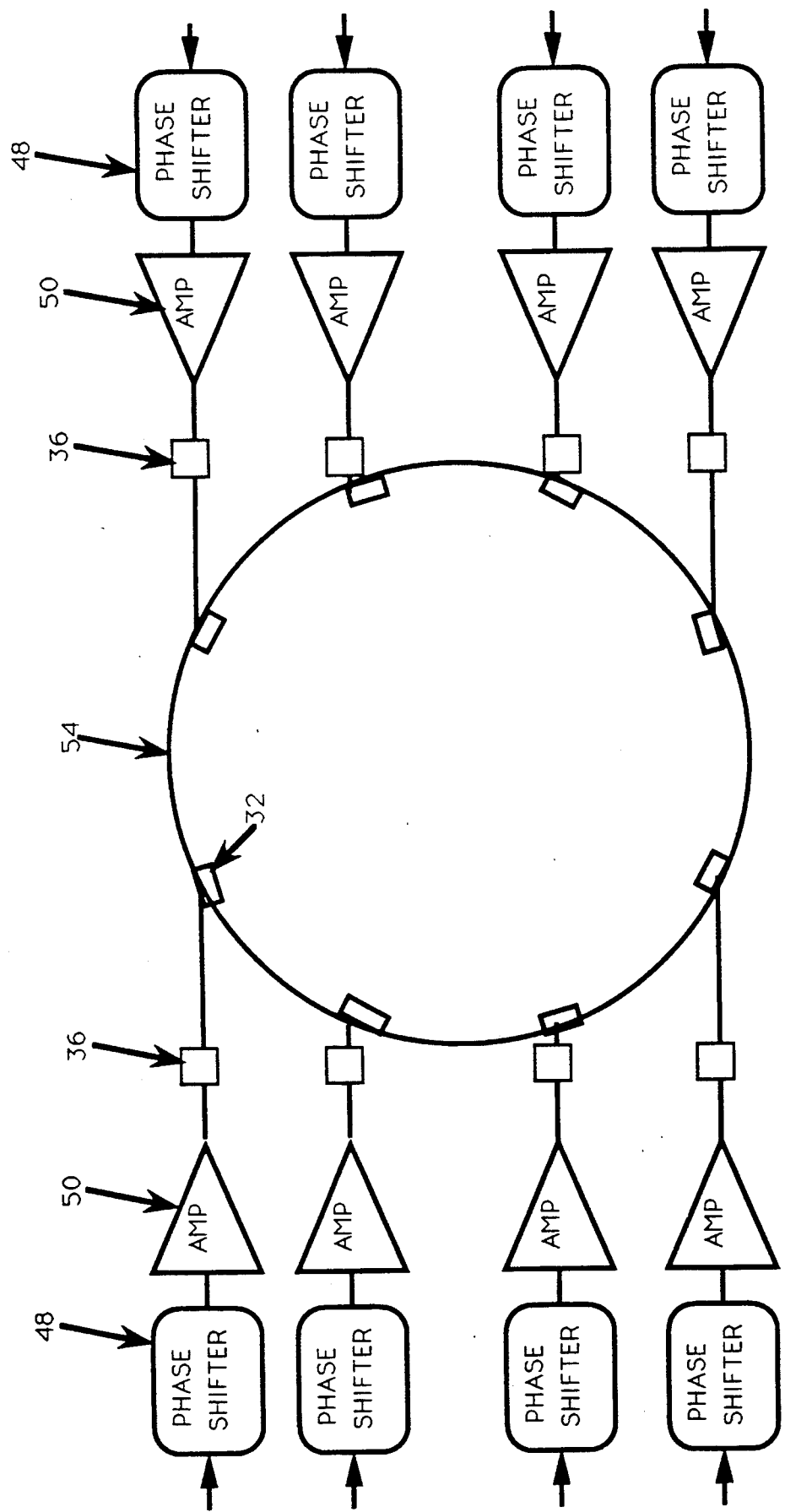
FIG. 6 is a partial schematic view showing in block form a second power connector arrangement for the eight groups of dipole antennae of FIG. 2.

If an eight channel amplifier is used (FIG. 6), then the 4 two-way power dividers 52 of FIG. 5 are removed, and each antenna group 32 is connected directly to the connector assembly 36. Thus, the central dipoles phase would still be settable by either cable length changes (FIG. 3) or by adjustable phase shifters (FIG. 4).

Figure 7:
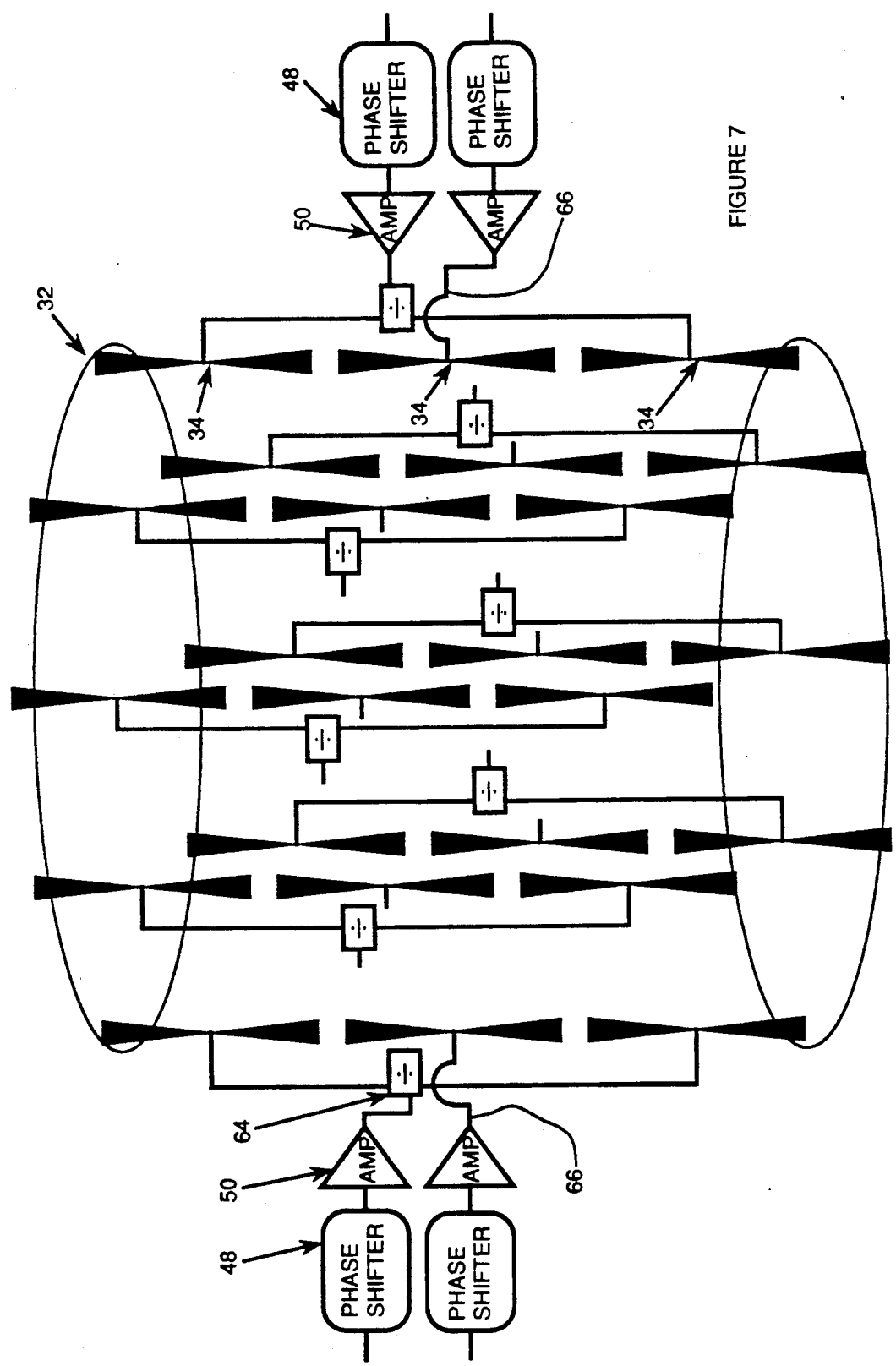
FIG. 7 is a partial schematic view showing in block form a third power connector arrangement for the eight groups of dipole antennae of FIG. 2.

When a sixteen channel amplifier is used (FIG. 7), the connector assembly 36 used to connect the three dipoles of each group would not be used. In lieu thereof each of the center dipoles of the eight groups 32 are connected directly to an amplifier of the sixteen channel amplifier of the signal modifier 16. The outer dipoles are connected in groups of two through two-way power dividers 64 to the remaining eight amplifiers 50 of the sixteen channel amplifier. The phase of the respective dipoles is set by the phase shifters 48 connected to the sixteen channel amplifiers. It will be appreciated by those skilled in the art that this arrangement will not provide long axis steering unless the phase to the end antennae are made to be different for grouped pairs.

Figure 8:
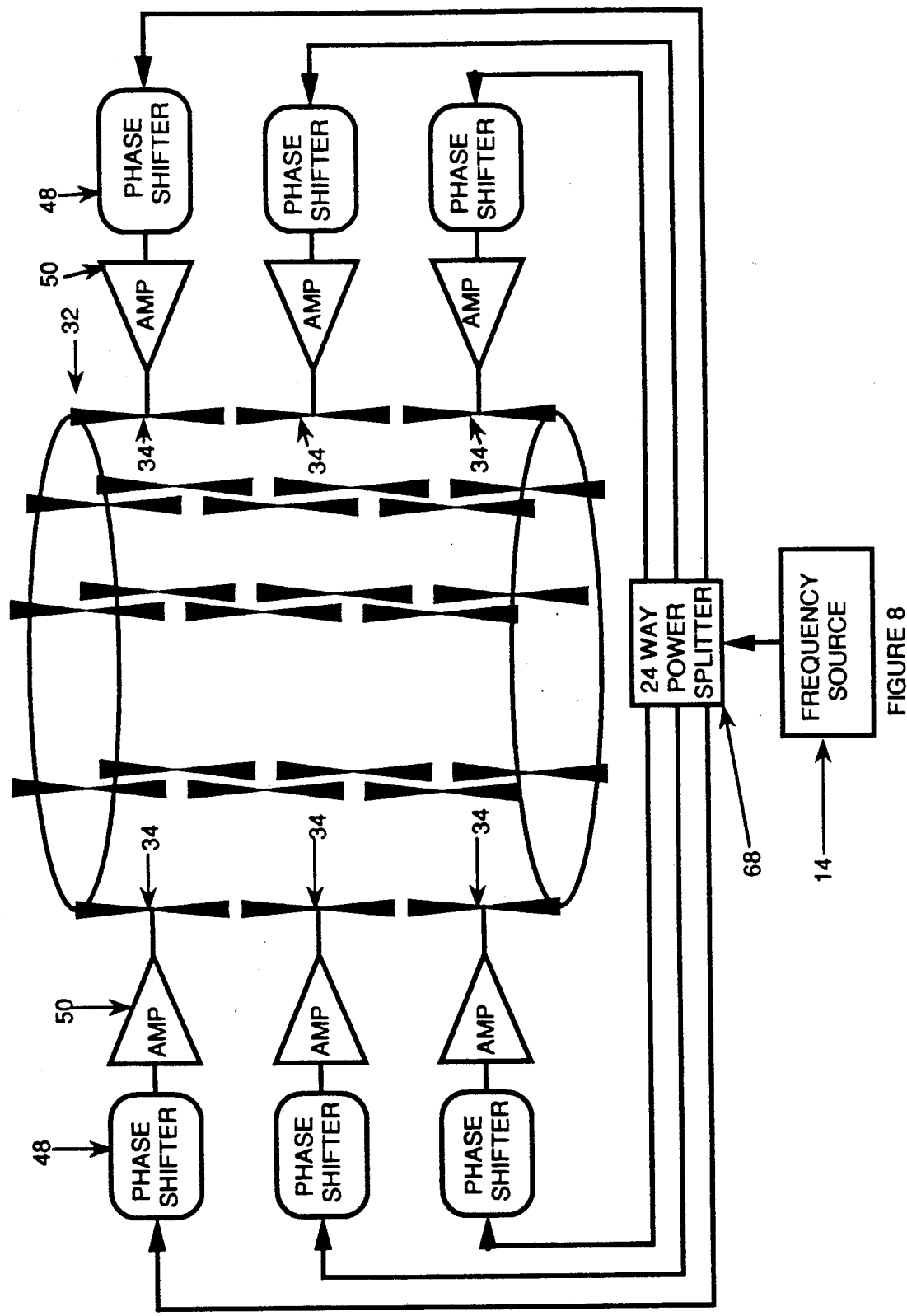
FIG. 8 is a schematic view showing in block form a fourth power connector arrangement for the eight groups of dipole antennae of FIG. 2.

For the 24 amplifier system (FIG. 8), the connector assembly 18 is omitted. A 24-way power splitter 68 is connected to the controller 14 for dividing the frequency source, and each signal modifier circuit 16 has a phase shifter 48 and an amplifier 50 connected to one of the 24 dipoles 34 of the eight groups 32. For deepest target heating the frequency of all antennae should be the same. However, different or changing frequencies, powers, or phases can be varied to obtain desired heating patterns. The change in frequencies will change surface heating. This is desirable when the target is located along the surface region. The control of these parameters would enable optimal treatments with these EM heating phased arrays.

Figure 9:
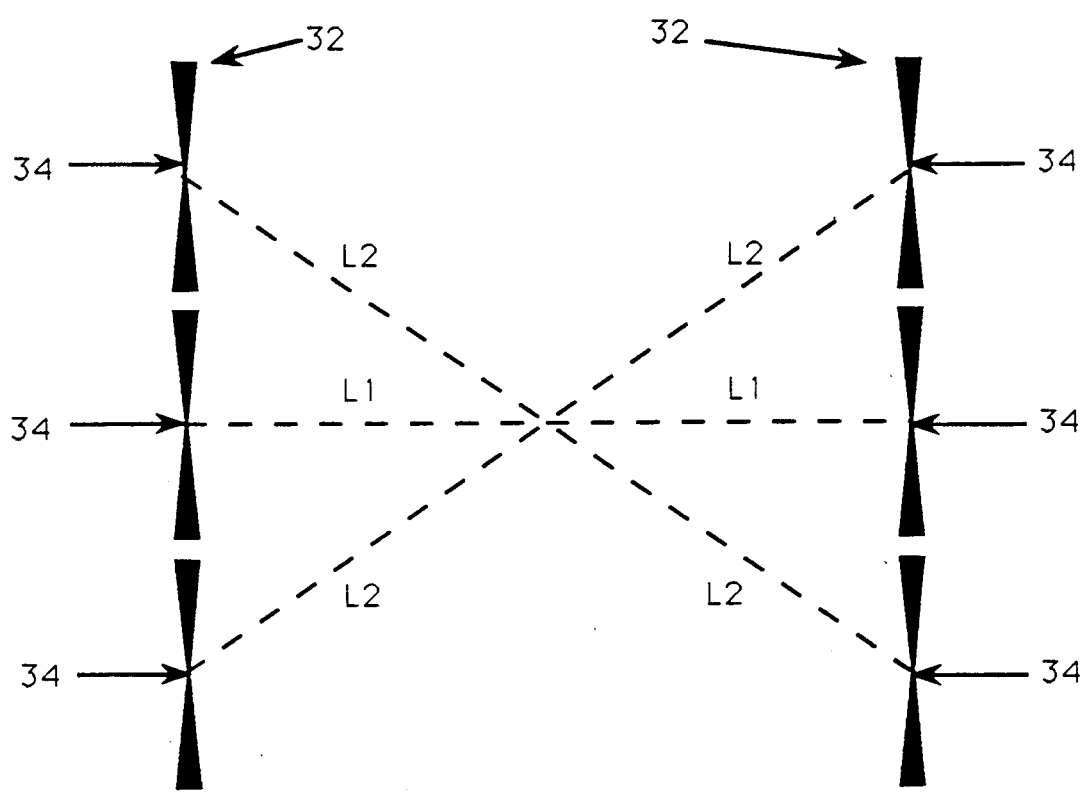
FIGS. 9-11 are views showing the paths of travel for various phase settings for the dipoles of the groups of antennae of FIG. 2 of which only two opposing groups are shown as being representative of the groups.
Figure 10:
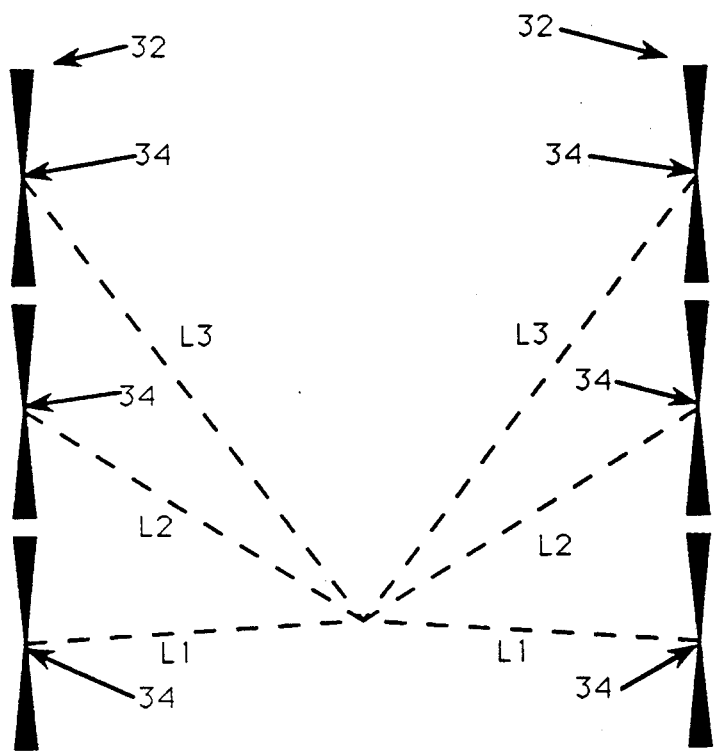
Figure 11:
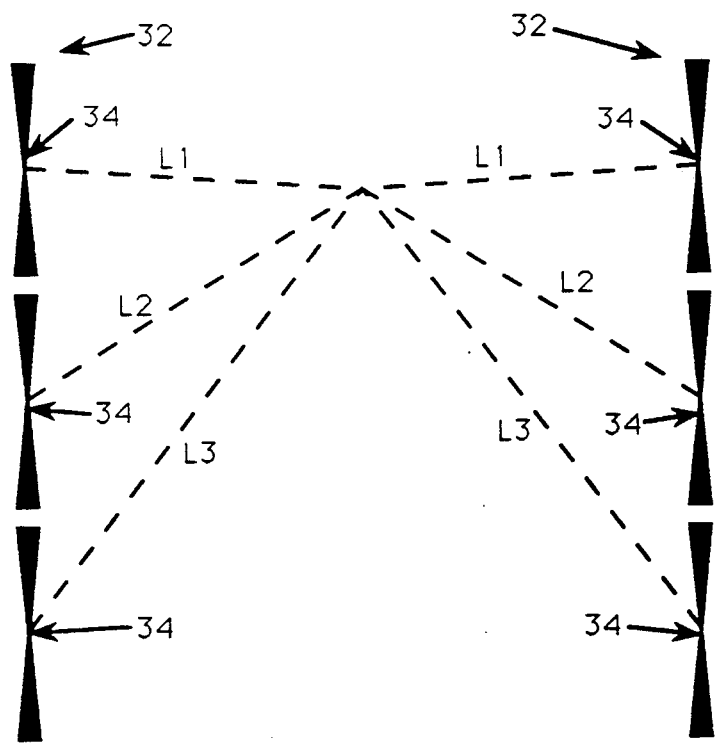

Referring now to FIGS. 9-11, FIG. 9 shows the path of travel for the EM radiation traveling from the dipoles toward the central heating zone. For clarity only two opposing groups 32 of electrodes 34 are shown as typical of the preferred eight groups. The lengths of the paths are designated by the distances $L_1$ and $L_2$. Path $L_1$ represents the path traveled by the energy leaving the central dipole for the central focus. $L_2$ represents the corresponding path lengths for the energy leaving the outer dipoles for the central focus. To accomplish maximal central energy focus and minimal long axis heating the activation phase of the central antennae should lag that of the end antennae by the difference of the equivalent phase delays of the paths $L_1$ and $L_2$. If $L_1$ and $L_2$ were assumed to be totally within a water bolus, at 100 MHz the water wavelength is 30 cm.s. Thus, the difference of $L_2-L_1$ could be divided by the wavelength and multiplied by 360 degrees to find the phase lag setting for the central antennae.

*Central Phase Setting* = $(L_2-L_1)*(360)/wavelength$, *degrees phase lag.*

FIG. 10 shows that if the phase of each antenna 34 is adjusted to obtain the same radiated phase at an offset position along the central axis that the radiated phase of paths $L_1$, $L_2$, and $L_3$ must be adjusted to arrive in phase at the off-set target. The result is that if the phase has been optimized for the off-set central focal zone that the heating will become more focused in the offset zone represented by FIG. 10. Thus, to steer the heating field focal zone along the long axis as shown in FIG. 11, it is necessary to adjust the phase of the power of each antenna to obtain the same radiated phase at an off-set position to the central zone along the long axis. This is in addition to steering the focal point along the cross-sectional axis as previously described in the parent application.

Each of the above described heating configurations, can be operated with a radiometric non-invasive temperature sensor by the addition of coaxial switches at the common coaxial tee locations. This would be at the tee of FIG. 3 and the power divider 44 of FIG. 4. The transmit system of FIG. 8 has no power splitting devices following the amplifiers, so there would be included 24 radiometric switches and phase shifters in phase shifters assembly 21 to incorporate the radiometric non-invasive thermometry. Thus, for this system, a 24 port summing power combiner 24 is required. The transmit system of FIGS. 5, 6, and 7 have 4, 8, and 16 splitter or tee junctions to the amplifiers so a corresponding number of switches are required for each to connect to the combiner. The phase shifter assembly 21 operates with the phase fixed, controlled, or adjustable to enable the phase focus of radiometric reception to be set at common locations within the body being heated. The radiometric mode is enabled by the closure of at least some of the switches within the phase shifter assembly 21 to the radiometer. The transmitted power is interrupted by the switches to avoid interference to the sensitive radiometric receivers.

Figure 12:
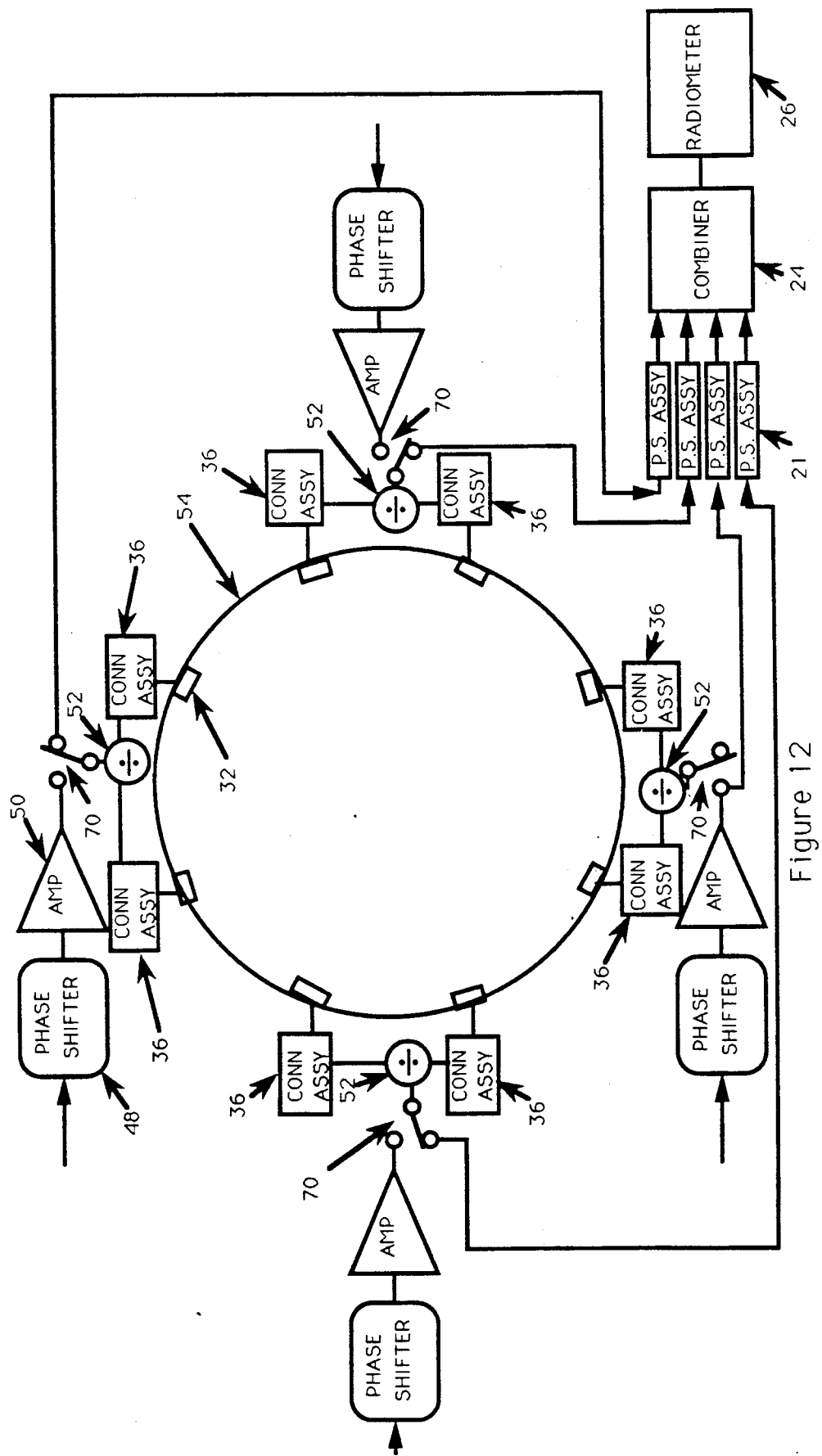
FIG. 12 is a view showing the addition of the radiometric receiver to the first power connector arrangement of FIG. 5.

FIG. 12 shows the addition of the radiometric receiver channels to the four channel system configuration of FIG. 5. As shown in FIG. 12 the switch 70 is a single pole two contact switch for switching between the heating power circuit and the radiometric circuit. The switches are placed between the amplifiers 50 and the power dividers 52 for the dipole groups 32 to avoid common phase shifting devices for both the transmit and received modes, unless these devices are very low loss such as coaxial cable. Otherwise, the added noise of a hot high powers phase shifter may interfere with the accurate noninvasive temperature measurement.

Some of the switching functions of the switching assembly 20 may be incorporated with the phase shifter assembly 21 to deactivate the connection of certain of the antenna group 32 (within the overall antenna group 22) to the power combiner to cause selective non-invasive tissue temperature measurement in particular surface regions underlying the connected antenna groups 32. This flexibility of connection paths could be within the switching assembly 20 or within the phase shifter assembly 21. Such switching is under the control of the controller 12 as indicated by the lead between the controller and the switching assembly of FIG. 1. Similarly the controller through the switching assembly 20 to the phase shifter 21 for controlling the phase shifter assembly.

Although several embodiments of this invention have been described, it will be apparent to a person skilled in the art that various modifications to the details of construction shown and described may be made without departing from the scope of this invention.

What is claimed is:

1. A hyperthermia apparatus having a three-dimensional focusing capability comprising:
   a first means for generating electromagnetic energy at preselected frequencies, phase and power levels;

a second means connected to the first means for receiving the electromagnetic energy from the first means and distributing it to a third means, said second means including means for adjusting relative phases of electromagnetic energy distributed to portions of the third means; and a third means connected to the second means and positioned for focusing the received electromagnetic energy to form a target heating spot selectively located within a body portion surrounded by the third means including spot size or location in the direction of the long axis of the body portion whereby three-dimensional location of the target heating spot is provided.

2. A hyperthermia apparatus according to claim 1 wherein the first means for generating electromagnetic energy at preselected frequencies, phase and power levels includes a power splitting means for dividing electromagnetic energy for a plurality of channels, a plurality of power amplifying means connected to the power splitting means for setting the power gain for each channel, and a corresponding plurality of phase shifting means connected to the power amplifying means for setting the power phase for each channel.

3. A hyperthermia apparatus according to claim 2 wherein the plurality of power amplifying means of the first means is a four channel amplifier, the power splitting means is a four-way power splitter, wherein the third means includes a plurality of antenna groups, each group including at least three antennae stacked in the direction of the long axis of the body portion surrounded by the plurality of antenna groups, and further including a power divider connected to each amplifier for dividing the power between the antennae groups of the third means.

4. A hyperthermia apparatus according to claim 2 wherein the plurality of power amplifying means of the first means is an eight channel amplifier and the power splitting means is an eight-way power splitter connected to the eight channel amplifier.

5. A hyperthermia apparatus according to claim 2 wherein the plurality of power amplifying means of the first means is a twenty-four channel amplifier, and the power splitting means ia a 24-way power splitter.

6. A hyperthermia apparatus according to claim 2 wherein the plurality of power amplifying means is a sixteen channel amplifier, the power splitting means is a sixteen-way power splitter, and wherein eight antenna groups form the third means and each include three dipole antennae stacked end to end, and wherein eight amplifiers of the sixteen channel amplifier are connected directly to the centrally located antenna of the eight antenna groups, and the remaining eight amplifiers are connected to eight two-way power dividing means, each of the two-way power dividing means being connected to the opposing end dipoles of an antenna group, and the phase of the opposing end antennae for each of the antenna groups being made different than the phase of the centrally located antenna of that group for the adjustment of the heating spot size in the direction of the long axis.

7. A hyperthermia apparatus according to claim 1 wherein the second means includes an electromagnetic energy connector means connecting the electromagnetic energy received from the first means to the third means, the means in said electromagnetic energy connector means for adjusting the phases of electromagnetic energy distributed to portions of the third means including an energy splitting means for splitting the energy received from the first means, and a plurality of electromagnetic energy conductors connected between the energy splitting means and the third means and having preselected lengths for producing energy outputs having phases corresponding to the lengths of the plurality of electromagnetic energy conductors for use by the third means for focusing the electromagnetic energy to form a target heating spot selectively located within the body portion surrounded by the third means including location in the direction of the long axis of the body portion.

8. A hyperthermia apparatus according to claim 1 wherein the second means includes an electromagnetic energy connector means connecting the electromagnetic energy received from the first means to the third means, the means in said electromagnetic energy connector means for adjusting the phases of electromagnetic energy distributed to portions of the third means including an energy splitting means for splitting the energy received from the first means, a plurality of electromagnetic energy conductors connected between the energy splitting means and the third means and having preselected lengths for producing energy outputs having phases corresponding to the lengths of the plurality of electromagnetic energy conductors, and a phase shifting module connected to the energy splitting means intermediate at least one of the plurality of electromagnetic energy conductors for setting the phase of the energy output of said at least one of the plurality of electromagnetic energy conductors, the energy outputs from the electromagnetic energy conductors for use by the third means in focusing the electromagnetic energy for locating a target heating spot selectively within the body portion surrounded by the third means including location in the direction of the long axis of the body portion.

9. A hyperthermia apparatus according to claim 1 wherein the third means includes a plurality of antenna groups, each group including at least three antennae stacked in the direction of the long axis of the body portion surrounded by the plurality of antenna groups, each of the at least three antennae being connected to the second means to receive electromagnetic energy of selected phases therefrom.

10. A hyperthermia apparatus according to claim 9 wherein the antennae of the plurality of antenna groups are selected from the group consisting of dipole, patch, metal strip, metallic waveguide, dielectric waveguides, resonant cavities, coaxial antennae, and TEM mode horns.

11. A hyperthermia apparatus according to claim 10 wherein the plurality of antenna groups includes eight antenna groups, each group including three dipole antennae stacked end to end.

12. A hyperthermia apparatus according to claim 1 further including a radiometric means connected to the third means for measuring energy radiating from the body portion surrounded by the third means for determining noninvasively the temperature of the target heating spot and its surrounding media.

13. A hyperthermia apparatus according to claim 12 wherein the radiometric means includes a switching means connected between the second and third means for connecting the third means selectively to the second means for receiving electromagnetic energy and to the radiometric means for receiving the energy radiating from the body portion through the third means, a radiant energy phase assembly connected to the switching means for adjusting the phase of the radiant energy received, a combiner connected to the radiant energy phase assembly for combining the radiant energy signals received, and a radiometer connected to the combiner for measuring the radiant energy signals from the combiner for determining the temperature of the target heating spot.

14. A hyperthermia apparatus according to claim 1 wherein the third means includes a plurality of antenna groups mounted upon a tube of dielectric material, and further including a temperature sensor adapted to be inserted into the heated area for sensing the temperature of the heated target, and temperature monitor means coupled to the temperature sensor for monitoring the sensed temperature of the temperature sensor and supplying signals to the first means to control operation of the first means.

15. A hyperthermia apparatus according to claim 1 including a control means connected to the first means for controlling the frequency, phase, and power levels of the output of the first means.

16. A hyperthermia apparatus according to claim 1 further including a radiometer means connected to the third means for measuring the energy radiating from the target heating spot through the third means, and a temperature monitoring means connected to the third means for monitoring the temperature of the target heating spot and a control means connected to the radiometer means and temperature monitoring means and to the first means for controlling phase and power level output of the first means responsive to the outputs of the radiometer means and temperature monitoring means.

17. A hyperthermia apparatus having a three-dimensional focusing capability for creating heating within a selected zone to be heated in a target, comprising:
 a plurality of electromagnetic energy applicators arranged in groups radially spaced around a target having a longitudinal axis, each group including a plurality of applicators spaced along the longitudinal axis of the target;
 means for supplying electromagnetic energy to the applicators;
 means for controlling the relative phase of electromagnetic energy supplied to respective groups of applicators whereby the zone to be heated within the target may be selectively sized and positioned radially within the target; and
 means for controlling the relative phase of electromagnetic energy supplied to respective applicators within a group of applicators whereby the zone to be heated may be selectively sized and positioned along the longitudinal axis of the target.

18. A hyperthermia apparatus according to claim 17 wherein the means for controlling the relative phase of electromagnetic energy supplied to respective applicators within a group of applicators includes an energy splitting means associated with each group of applicators adapted to receive electromagnetic energy from the means for supplying electromagnetic energy and for splitting the energy from the means for supplying electromagnetic energy, and a plurality of electromagnetic energy conductors connected between each energy splitting means and respective applicators of the associated group of applicators, said electromagnetic energy conductors having preselected lengths for producing energy outputs to connected applicators having phases dependent upon the lengths of said conductors.

19. A hyperthermia apparatus according to claim 17, wherein the means for controlling the relative phase of electromagnetic energy supplied to respective applicators within a group of applicators includes means connecting the means for supplying electromagnetic energy to respective applicators of a group of applicators, and a phase shift means connected to at least one of the plurality of applicators to shift the phase of energy supplied to that one applicator relative to the phase of energy supplied to other applicators in the group.

20. A hyperthermia apparatus according to claim 17, wherein there are three applicators in each group of applicators.

21. A hyperthermia apparatus according to claim 17, wherein there are eight groups of applicators.

22. A hyperthermia apparatus having a three-dimensional focusing capability for creating heating within a selected zone to be heated in a target, comprising:
 electromagnetic energy applicator means radially surrounding a target having a longitudinal axis and extending partially along the longitudinal axis of the target, said applicator means adapted to supply electromagnetic energy to the target;
 Means for supplying electromagnetic energy to the applicator means to be supplied to the target; and
 Means for controlling the relative phase of electromagnetic energy supplied to the target from different portions of the applicator means so as to focus the electromagnetic energy in the target to form a heating zone selectively sized and located with respect to three dimensions within the target.

* * * * *